United States Patent [19]

Kamatani et al.

[11] 4,412,072

[45] Oct. 25, 1983

[54] ISOCYANATE COMPOSITION

[75] Inventors: Yoshio Kamatani; Noriaki Fujita, both of Osaka, Japan

[73] Assignee: Takeda Chemical Industries, Ltd., Osaka, Japan

[21] Appl. No.: 270,118

[22] Filed: Jun. 3, 1981

[30] Foreign Application Priority Data

Jun. 23, 1980 [JP] Japan .................................. 55-85487

[51] Int. Cl.$^3$ .......................................... C07D 273/04
[52] U.S. Cl. ..................................................... 544/68
[58] Field of Search .......................................... 544/68

[56] References Cited

U.S. PATENT DOCUMENTS 2,196,751  4/1940  Dickey et al. ........................ 544/68
3,238,200  3/1966  Berstein et al. ...................... 544/68

FOREIGN PATENT DOCUMENTS 48-15275  4/1973  Japan .

*Primary Examiner*—John M. Ford
*Attorney, Agent, or Firm*—Antonelli, Terry & Wands

[57] ABSTRACT

Isocyanate composition which is superior in stability and reactivity, wherein at least one additive selected from the group consisting of peroxides, sulfur, polysulfides, metal sulfides and halogens is added to a reaction product of organic isocyanate and carbon dioxide in an amount of 0.001 to 10% by weight based on the starting isocyanate.

39 Claims, No Drawings

ISOCYANATE COMPOSITION

This invention relates to an isocyanate composition having, in combination, improved stability and high reactivity, which comprises the reaction product of organic isocyanates with carbon dioxide and at least one additive selected from the group consisting of peroxides, sulfur, polysulfides, metal sulfides and halogens.

Heretofore, it is known that an organic isocyanate compound reacts with carbon dioxide in the presence of a catalyst to give a reaction mixture containing an isocyanate having an oxadiazinetrione ring structure. And, in order to terminate the reaction and to ensure a sufficient shelf life of the resulting mixture produced, it has been proposed to add some or other additives to the reaction mixture. Among such reaction terminating and stabilizing agents known to be effective, there are alkylating agents, acylating agents, acids, ester derivatives, phenols, etc., such as dimethyl sulfate, methyl iodide, toluenesulfonic acid, benzoyl chloride, ethyl chloroformate, phosphorus trichloride, boron trifluoride etherate, pentachlorophenol, monochloroacetic acid, ethyl α-bromopropionate, picric acid, 2,4,6-trinitrobenzoic acid and the like (see, for example, Derwent Abstract No. J74015-275).

The inventors have found that these known reaction terminating and stabilizing agents, however, degrade reactivity of the produced oxadiazinetrione ring with a hydroxy or amino compound and furthermore, the known agents often give unfavorable influences to terminal NCO groups in the product. A new additive that can terminate the formation of oxadiazinetrione as well as can ensure a sufficient shelf life of the resulting composition without any decrease of the reactivity of the reaction product with hydroxy or amino compounds, has been expected.

The object of this invention is to provide a new composition to satisfy the above requirement.

According to this invention, an isocyanate composition is provided, which contains the reaction product of organic isocyanates and carbon dioxide and at least one additive selected from the group consisting of peroxides, sulfur, polysulfides, metal sulfides and halogens.

First, explanation is given below on the reaction product of organic isocyanates with carbon dioxide:

The organic isocyanates which can be employed in this invention include aliphatic, alicyclic and aromatic-aliphatic isocyanates. Examples of the aliphatic isocyanate may, for example, be methyl isocyanate, ethyl isocyanate, n-butyl isocyanate, ω-chlorohexyl isocyanate, tetramethylene diisocyanate, hexamethylene diisocyanate, ω,ω'-diisocyanatodipropyl-ether, 2,6-diisocyanatocaproic acid ester, 1,6,11-triisocyanatoundecane, etc. The alicyclic isocyanate may, for example, be cyclohexyl isocyanate, cyclohexylmethyl isocyanate, bis(isocyanatomethyl)cyclohexane, bis(isocyanatoethyl)cyclohexane, 1-isocyanato-3-isocyanatomethyl-3,5,5-trimethylcyclohexane, bis(4-isocyanatocyclohexyl)methane, etc. The aromatic-aliphatic isocyanate may, for example, be benzyl isocyanate, xylylene diisocyanate, bis(2-isocyanatoethyl)benzene, etc. Among the organic isocyanates defined above, an organic polyisocyanate is preferably employed, specifically bis(isocyanatomethyl)cyclohexane or hexamethylene diisocyanate. These isocyanates can also be used as a mixture of two or more different isocyanates.

The isocyanates may also be prepolymer having a terminal NCO group, which can be derived from the reaction of a polyisocyanate having two or more NCO groups in a molecule among above-mentioned organic isocyanates with a polyol, e.g., ethylene glycol, propylene glycol, diethylene glycol, 1,4-butanediol, glycerin, trimethylolpropane, polyether polyol, polyester polyol, etc. or a polyamine, e.g. ethylenediamine, hexamethylenediamine, phenylenediamine, polyether polyamine, etc. Furthermore, polyisocyanates, wherein some of the isocyanate groups have been dimerized, trimerized or blocked with a blocking agent, can also be employed.

The reaction of the organic isocyanates with carbon dioxide is carried out in the presence of a catalyst. The preferred catalysts are such tertiary phosphorous compounds as triethylphosphine, tri-n-butylphosphine, dimethylphenylphosphine, diethylcyclohexylphosphine, 1-ethylphospholane, 1-n-butylphosphane, etc. Arsenic compounds such as tri-n-butylarsine, triphenylarsine oxide, etc., and hydroquinone compounds such as hydroquinone, anthrahydroquinone, etc. are also employable as a catalyst. The amount of the catalyst varies in the range of about 0.001–10 weight %, preferably about 0.01–3 weight %, depending on the catalyst, reaction conditions and the isocyanate compound employed.

Any form of carbon dioxide, one of reactants, may be used as long as even a part thereof can be dissolved in the reaction mixture. For example, $CO_2$ gas may be bubbled into the reaction mixture or solid $CO_2$ may be made copresent in the reaction mixture. Alternatively, gaseous or liquefied $CO_2$ may be introduced under pressure.

The reaction is carried out in the presence or absence of a solvent. Any solvent, that does not interfere with the reaction, can be used; e.g. cyclohexane, toluene, ethyl acetate, methyl ethyl ketone, tetrahydrofuran, cellosolve acetate etc. Since the viscosity of the reaction mixture increases gradually as the reaction proceeds, it may prove useful to add a solvent on the way of reaction in order to control the viscosity.

The reaction temperature may range usually from −70° C. to +150° C., depending on the starting isocyanate and the catalyst employed. Since side reactions such as polymerization of the isocyanate often occur at high temperatures, the reaction is preferably carried out within the range of −20° to +100° C.

To the reaction product thus obtained is added at least one additive selected from the group consisting of peroxides, sulfur, polysulfides, metal sulfides and halogens.

The peroxides may be inorganic or organic compounds, e.g. perchloric acid, sodium perborate, ammonium persulfate, hydrogen peroxide, t-butyl hydroperoxide, cumene hydroperoxide, benzoyl peroxide, acetyl peroxide, succinoyl peroxide, methyl ethyl ketone peroxide, cyclohexanone peroxide, di-t-butyl peroxide, dicumyl peroxide, t-butyl peracetate, t-butyl perbenzonate, acetyl(cyclohexanesulfonyl)peroxide, diisopropyl peroxycarbonate, peracetic acid, perbenzoic acid, permaleic acid, etc. The sulfur may be crystalline, amorphous or liquid.

The polysulfide may be a compound having an S-S bond, e.g. ethyl disulfide, phenyl disulfide, γ-oxypropyl disulfide, β,β'-dithiodipropionic acid, benzoyl disulfide, bis(diethylcarbamoyl)disulfide, bis(pentamethylenethiocarbamoyl)tetrasulfide, 2-(cyclohexyldithio)benzimidazole, bis(isopropoxythioyl)disulfide, etc.

The metal sulfide may be compound which has metal and sulfur atoms, e.g. zinc dibutyldithiocarbamate, 2-mercaptobenzothiazole sodium salt, 2-mercaptobenzimidazole nickel salt, etc.

The halogens include fluorine, chlorine, bromine and iodine, among which chlorine and bromine are preferred from workability and economic views.

Among the additives defined above, peroxides, sulfur or polysulfides are preferably employed. The most preferred are peroxides, particularly organic peroxides.

Each of these additives is sufficiently effective, but two or more additives can also be used. Further, a compound capable of forming one of said additives in situ may also be employed.

In order to terminate the reaction between the isocyanates and carbon dioxide and to stabilize the reaction product, said additive or additives are usually added at the time when the reaction system has attained a predetermined conversion rate. The intended conversion rate can be determined by a sequential titrimeric measurement of NCO content in the reaction mixture, an NMR method involving a comparison of the peak intensity of the hydrogen atom bound to the carbon atom adjacent to the NCO group with that of the hydrogen atom bound to the carbon atom directly bonded to the oxadiazinetrione ring, a viscometric analysis, or a chromatographic analysis of a residual amount of starting organic isocyanate.

The amount of the additive ranges from 0.001 to 10 weight %, preferably from 0.01 to 3 weight % based on the weight of the isocyanates used as a starting material, while depending on the quantity and species of the isocyanates and the catalyst used.

While said additive is preferably soluble in the reaction mixture, it is possible to use the additive as dissolved in a solvent or to raise the temperature of the reaction mixture to increase the solubility of the additive. If necessary, the reaction mixture may be heated with the additive for a while to completely terminate the reaction and to enhance the stabilizing effect of the objective composition.

When, for example, a diisocyanate is employed, the reaction product presumably has the following structure:

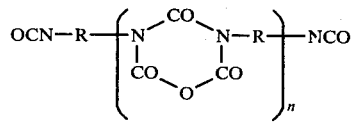

[wherein R is the residue of the diisocyanate used and n is an integer of 1, 2, 3, 4 . . . ].

The product of the above reaction is in the form of a mixture of polyisocyanates having various values for n, usually accompanying the starting organic isocyanates. The polyisocyanates having 0.01 to 5, preferably 0.1 to 5, in average of the symbol n, are particularly suitable for production of polyurethane.

After the reaction is terminated, the stabilized isocyanates composition, said isocyanates containing oxadiazinetrione rings, if necessary, can be purified by removing the unreacted monomeric isocyanates from the reaction mixture by such procedure as distillation, extraction, crystallization, etc. An additional amount of the aforementioned additive can also be added, if necessary, before or after the separation procedure.

The isocyanate composition thus obtained, said isocyanate containing oxadiazinetrione rings, features an excellent reactivity with hydroxy and amino compounds as well as a longer shelf life. Therefore, the reaction of the oxadiazinetrione ring to form allophanate or biuret compounds can be carried out at low temperature and in high yield.

The isocyanate composition containing the reaction product prepared from polyisocyanates having two or more NCO groups in its molecule, the said reaction product having two or more functional groups in the total of oxadiazinetrione groups and isocyanate groups, can be used for the production of polyurethane resin or polyurethane prepolymer by subjecting the composition to a reaction with a polyhydroxy compound or polyamino compound. In this reaction, because of the high reactivity of the oxadiazinetrione rings with hydroxy compounds or amino compounds, the reaction temperature can be lowered, even if the reaction needs heating. Furthermore, the reaction can also be conducted at a lower temperature even when a tertiary amine, an inorganic acid salt of a metal, or an organometallic compound is present in a small amount to the reaction mixture.

By using these characteristics, the isocyanate composition of this invention can be used as a starting material in the production of polyurethane resins suited for coatings, adhesives, moldings, foams, etc.

For a further understanding of this invention, examples are given below.

EXAMPLE 1

While introducing carbon dioxide gas into 291 g of 1,3-bis(isocyanatomethyl)cyclohexane at 10° C. at the rate of 400 ml/min., the reaction was allowed to proceed under stirring with the addition of 3.0 g of tri-n-butylphosphine. After 8 hours, the carbon dioxide feed was stopped and 4.0 g of benzoyl peroxide was added to the reaction mixture so as to terminate the reaction. The weight of the product was greater by 29 g than the weight of the original reaction system and the NCO content of the reaction mixture was 19.3%.

100 g of the product was mixed with 741 g of acrylic polyol, Acrydic A-801 (OH value: 50, non-volatile matter: 50%, a product of Dainippon Ink and Chemicals Inc.), and the mixture was diluted with ethyl acetate and divided into two equal parts. In one of these two parts, 50 mg of dibutyltin dilaurate was dissolved. Each of the divided two parts was sprayed on a cold rolled steel panel, followed by heating for 20 minutes to produce a film about 40μ thick. The cure temperatures of such films are shown in Table 1.

As a comparative example, 2.5 g of dimethyl sulfate was added to the reaction mixture, instead of benzoyl peroxide, after the reaction. This sample was sprayed and cured in the same manner as above. The results are also shown in Table 1.

TABLE 1

| Additive | Benzoyl peroxide | | Dimethyl sulfate | |
|---|---|---|---|---|
| Curing Catalyst | Absent | Present | Absent | Present |
| Curable temperature (°C.) | 130 | 110 | 140 | 130 |

EXAMPLE 2

While introducing carbon dioxide gas into 168 g of hexamethylene diisocyanate at 50° C. at the rate of 300 ml/min., the reaction was allowed to proceed under stirring with the addition of 1 g of tri-ethylphosphine for 6 hours. Then, the carbon dioxide feed was stopped and 0.3 g of sulfur powder was added to the reaction mixture. After stirring for a further 30 minutes, the reaction mixture was cooled. The weight of the reaction mixture was greater by 20 g than the weight of the original reaction system and the NCO content of the mixture was 22.6%.

The reaction mixture was dissolved in 100 g of methyl isobutyl ketone, and 111 g of triethylene glycol and 20 mg of stannous octoate were added to the solution, followed by allowing the reaction to proceed at 80° C. for two hours.

The reaction product was divided into two equal parts and 45 mg of 1,3-diacetoxytetrabutyl distannoxane was added to one of these two parts.

Each of these divided two parts was applied onto a glass plate, followed by heating for 20 minutes.

As a comparative example, 0.9 g of ethyl bromoacetate was added to the reaction mixture, instead of the sulfur powder. This sample was treated in the same manner. The results are also shown in Table 2.

TABLE 2

| Additive | Sulfur | | Ethyl bromoacetate | |
|---|---|---|---|---|
| Curing Catalyst | Absent | Present | Absent | Present |
| Curable temperature (°C.) | 150 | 130 | 170 | 150 |

EXAMPLE 3

An autoclave of 1 l capacity was charged with 336 g of hexamethylene diisocyanate into which carbon dioxide was introduced under stirring. After the addition of 2.0 g of tri-n-butylphosphine, the mixture was reacted at 20°–30° C. while the pressure of $CO_2$ was held at 4–5 kg/cm$^2$. After 8 hours, carbon dioxide gas was discharged from the autoclave and nitrogen gas was bubbled into the mixture. The weight of the reaction mixture was greater by 50 g than the weight of the original reaction system and the NCO content of the mixture was 16.5%.

The additives indicated in Table 3 were respectively added to 20 g samples of this reaction mixture, and each sample was heated under stirring. 5 g of each sample was dissolved in 10 g of diethyleneglycol dimethyl ether and a further 6.2 g of diethyleneglycol monomethyl ether was added. The mixture was reacted at 140° C. for 30 minutes.

The percentage of reacted oxadiazinetrione rings was determined from the infrared absorption at 1815 cm$^{-1}$. The result was shown in Table 3 along with the result of a similar reaction carried out with 2 mg of 1,3-diacetoxytetrabutyl distannoxane at 120° C. for 30 minutes. The viscosity changes of polyisocyanate samples containing various additives on storage at room temperature for a month are also shown in the Table 3.

TABLE 3

| Additive | Amount added (mg) | Reaction percentage of oxadiazinetrione (%) | | Viscosity change after 1 month |
|---|---|---|---|---|
| | | Without catalyst | With catalyst | |
| Cumene hydroperoxide | 110 | 77 | 85 | No change |
| Benzoyl peroxide (80%) | 140 | 80 | 78 | No change |
| Hydrogen peroxide (20% solution in t-BuOH) | 100 | 73 | 76 | No change |
| Methyl ethyl ketone peroxide (55%) | 100 | 72 | 72 | No change |
| t-Butyl peracetate (50%) | 160 | 68 | 75 | No change |
| Dicumyl peroxide | 170 | 70 | 70 | No change |
| Phenyl disulfide | 130 | 24 | 32 | No change |
| Bis(pentamethylenethiocarbamoyl)tetrasulfide | 50 | 30 | 40 | No change |
| Zinc dibutyldithiocarbamate | 280 | 35 | 44 | No change |
| Bromine (Comparative Example) | 100 | 53 | 65 | No change |
| Dimethyl sulfate | 100 | 4 | 5 | No change |
| Boron trifluoride etherate | 80 | 6 | 5 | No change |
| Trichloroacetic acid | 50 | 6 | 8 | Increases |
| Ethyl bromoacetate | 50 | 15 | 13 | No change |
| Benzoyl chloride | 80 | 11 | 7 | No change |
| p-Toluenesulfonyl chloride | 60 | 8 | 10 | Increases |
| Without Additive | — | — | — | Solidifies |

We claim:

1. A composition which comprises a stabilized reaction product of an organic isocyanate with carbon dioxide and at least one stabilizing additive selected from the group consisting of an organic peroxide, an inorganic peroxide, sulfur, a polysulfide compound having an S-S bond, a metal sulfide and a halogen; said stabilizing additive being admixed with the reaction product in an amount of 0.001 to 10% by weight based on the organic isocyanate at the time when the reaction product has obtained a predetermined conversion rate whereby the reaction product contains an isocyanate having a stabilized oxadiazinetrione ring structure.

2. The composition according to claim 1 wherein the organic isocyanate is an aliphatic, alicyclic or aromatic-aliphatic isocyanate.

3. The composition according to claim 1 wherein the organic isocyanate is an organic polyisocyanate.

4. The isocyanate composition according to claim 3 wherein the organic polyisocyanate is bis-(isocyanatomethyl)cyclohexane or hexamethylene diisocyanate.

5. The composition according to claim 1, wherein the additive is sulfur.

6. The composition according to claim 1, wherein the additive is an organic peroxide.

7. The composition according to claim 1, wherein the additive is an inorganic peroxide.

8. In a method for stabilizing a reaction product obtained from the reaction of an organic isocyanate with carbon dioxide wherein a stabilizing additive is added to the reaction product, the improvement which comprises utilizing as the stabilizing additive at least one member selected from the group consisting of an inorganic peroxide, an organic peroxide, sulfur, a polysulfide compound having an S-S bond, a metal sulfide and a halogen, said stabilizing additive being added to said reaction product in an amount of 0.001 to 10% by weight based on the organic isocyanate.

9. A method according to claim 8 wherein the organic isocyanate is an aliphatic, alicyclic or aromatic-aliphatic isocyanate.

10. A method according to claim 8 wherein the organic isocyanate is an organic polyisocyanate.

11. A method according to claim 10 wherein the organic polyisocyanate is bis(isocyanatomethyl)-cyclohexane or hexamethylene diisocyanate.

12. The composition according to claim 1, wherein the stabilizing additive is a polysulfide compound having an S-S bond.

13. The composition according to claim 1, wherein the stabilizing additive is a metal sulfide.

14. The composition according to claim 1, wherein the stabilizing additive is a halogen.

15. A method according to claim 8, wherein the stabilizing additive is added to said reaction product at the time when the reaction product has obtained a predetermined conversion rate.

16. A method according to claim 15 wherein the reaction of the organic isocyanate with carbon dioxide is effected in a reactor which is charged with the organic isocyanate and into which the carbon dioxide is introduced, the introduction of carbon dioxide being terminated prior to addition of the stabilizing additive, with the reaction being carried out within a range of $-20°$ to $+100°$ C.

17. A method according to claim 8, wherein the stabilizing additive is an organic peroxide.

18. A method according to claim 17, wherein the organic peroxide is t-butyl hydroperoxide, cumene hydroperoxide, benzoyl peroxide, acetyl peroxide, succinoyl peroxide, methyl ethyl ketone peroxide, cyclohexanone peroxide, di-t-tutyl peroxide, dicumyl peroxide, t-butyl peracetate, t-butyl perbenzonate, acetyl(cyclohexanesulfonyl)peroxide, diisopropyl peroxycarbonate, peracetic acid, perbenzoic acid or permaleic acid.

19. A method according to claim 17, wherein the organic peroxide is benzoyl peroxide.

20. A method according to claim 17, wherein the organic peroxide is cumene hydroperoxide.

21. A method according to claim 17, wherein the organic peroxide is methyl ethyl ketone peroxide.

22. A method according to claim 17, wherein the organic peroxide is t-butyl peracetate.

23. A method according to claim 17, wherein the organic peroxide is dicumyl peroxide.

24. A method according to claim 8, wherein the stabilizing additive is an inorganic peroxide.

25. A method according to claim 24, wherein the inorganic peroxide is perchloric acid, sodium perborate, ammonium persulfate or hydrogen peroxide.

26. A method according to claim 24, wherein the inorganic peroxide is hydrogen peroxide.

27. A method according to claim 8, wherein the stabilizing additive is sulfur.

28. A method according to claim 27, wherein the sulfur is crystalline, amorphous or liquid.

29. A method according to claim 8, wherein the stabilizing additive is a polysulfide compound having an S-S bond.

30. A method according to claim 29, wherein the polysulfide compound is ethyl disulfide, phenyl disulfide, $\gamma$-oxypropyl disulfide, $\beta,\beta'$-dithiodipropionic acid, benzoyl disulfide, bis(diethylcarbamoyl)disulfide, bis(pentamethylenethiocarbamoyl)tetrasulfide, 2-(cyclohexyldithio)benzimidazole or bis(isopropoxythioyl)-disulfide.

31. A method according to claim 29, wherein the polysulfide compound is phenyl disulfide.

32. A method according to claim 29, wherein the polysulfide compound is bis(pentamethylenethiocarbamoyl)tetrasulfide.

33. A method according to claim 8, wherein the stabilizing additive is a metal sulfide consisting of a compound having metal and sulfur atoms.

34. A method according to claim 33, wherein the metal sulfide compound is zinc dibutyldithiocarbamate, 2-mercaptobenzothiazole sodium salt or 2-mercaptobenzimidadole nickel salt.

35. A method according to claim 33, wherein the metal sulfide compound is zinc dibutyldithiocarbamate.

36. A method according to claim 8, wherein the stabilizing additive is a halogen.

37. A method according to claim 36, wherein the halogen is fluorine, chlorine, bromine or iodine.

38. A method according to claim 37, wherein the halogen is bromine or chlorine.

39. A method according to claim 37, wherein the halogen is bromine.

* * * * *